US012591982B2

(12) United States Patent
Gao et al.

(10) Patent No.: US 12,591,982 B2
(45) Date of Patent: Mar. 31, 2026

(54) MOTION DETECTION ASSOCIATED WITH A BODY PART

(71) Applicant: Shanghai United Imaging Intelligence Co., Ltd., Shanghai (CN)

(72) Inventors: Zhongpai Gao, Rowley, MA (US); Abhishek Sharma, Boston, MA (US); Meng Zheng, Cambridge, MA (US); Benjamin Planche, Briarwood, NY (US); Ziyan Wu, Lexington, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 344 days.

(21) Appl. No.: 18/195,009

(22) Filed: May 9, 2023

(65) Prior Publication Data

US 2024/0378731 A1 Nov. 14, 2024

(51) Int. Cl.
| | |
|---|---|
| *G06T 7/246* | (2017.01) |
| *A61B 5/11* | (2006.01) |
| *G06V 10/25* | (2022.01) |
| *G06V 10/44* | (2022.01) |

(52) U.S. Cl.
CPC ................ *G06T 7/246* (2017.01); *A61B 5/11* (2013.01); *G06V 10/25* (2022.01); *G06V 10/44* (2022.01); *G06T 2207/10024* (2013.01); *G06T 2207/10081* (2013.01); *G06T 2207/10088* (2013.01)

(58) Field of Classification Search
None
See application file for complete search history.

(56) References Cited

U.S. PATENT DOCUMENTS

| | | | | |
|---|---|---|---|---|
| 8,331,637 | B2 * | 12/2012 | Bar-Aviv | .............. G16H 50/20 |
| | | | | 382/128 |
| 10,319,209 | B2 | 6/2019 | Carlton-Foss | |
| 11,576,578 | B2 * | 2/2023 | Hao | .................... A61B 5/7485 |
| 2018/0193667 | A1 * | 7/2018 | Kaiser | ................. A61N 5/1049 |
| 2018/0300556 | A1 * | 10/2018 | Varerkar | .............. G06V 20/40 |
| 2019/0090785 | A1 | 3/2019 | Heinrich et al. | |
| 2020/0226827 | A1 * | 7/2020 | Kim | ......................... G06T 7/50 |
| 2021/0290106 | A1 | 9/2021 | Stever et al. | |

FOREIGN PATENT DOCUMENTS

| | | |
|---|---|---|
| CN | 110088643 B | 8/2019 |
| EP | 3492945 A1 | 6/2019 |

* cited by examiner

*Primary Examiner* — Nancy Bitar
(74) *Attorney, Agent, or Firm* — Zhong Law, LLC

(57) ABSTRACT

Detecting motions associated with a body part of a patient may include using an image sensor installed inside a medical scanner to capture first and second images of the patient inside the medical scanner, wherein the first image may depict the patient in a first state and the second image may depict the patient in a second state. A first area, in the first image, that corresponds to the body part of the patient may be identified and a second area, in the second image, that corresponds to the body part may also be identified so that a first plurality of features may be extracted from the first area of the first image and a second plurality of features may be extracted from the second area of the second image. A motion associated with the body part of the patient may be determined based on the first and second pluralities of features.

16 Claims, 7 Drawing Sheets

500

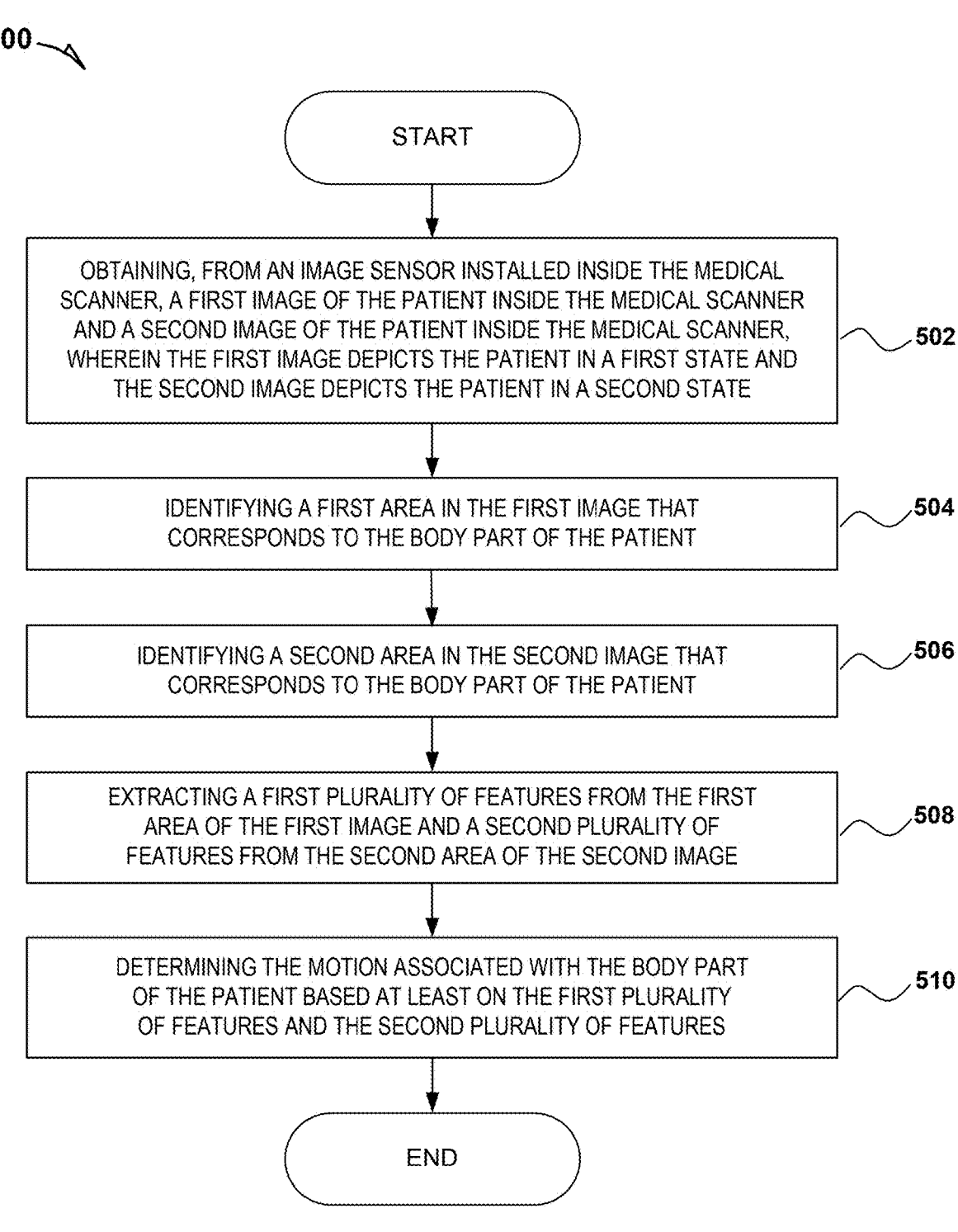

START

OBTAINING, FROM AN IMAGE SENSOR INSTALLED INSIDE THE MEDICAL SCANNER, A FIRST IMAGE OF THE PATIENT INSIDE THE MEDICAL SCANNER AND A SECOND IMAGE OF THE PATIENT INSIDE THE MEDICAL SCANNER, WHEREIN THE FIRST IMAGE DEPICTS THE PATIENT IN A FIRST STATE AND THE SECOND IMAGE DEPICTS THE PATIENT IN A SECOND STATE — 502

IDENTIFYING A FIRST AREA IN THE FIRST IMAGE THAT CORRESPONDS TO THE BODY PART OF THE PATIENT — 504

IDENTIFYING A SECOND AREA IN THE SECOND IMAGE THAT CORRESPONDS TO THE BODY PART OF THE PATIENT — 506

EXTRACTING A FIRST PLURALITY OF FEATURES FROM THE FIRST AREA OF THE FIRST IMAGE AND A SECOND PLURALITY OF FEATURES FROM THE SECOND AREA OF THE SECOND IMAGE — 508

DETERMINING THE MOTION ASSOCIATED WITH THE BODY PART OF THE PATIENT BASED AT LEAST ON THE FIRST PLURALITY OF FEATURES AND THE SECOND PLURALITY OF FEATURES — 510

END

*FIG. 5*

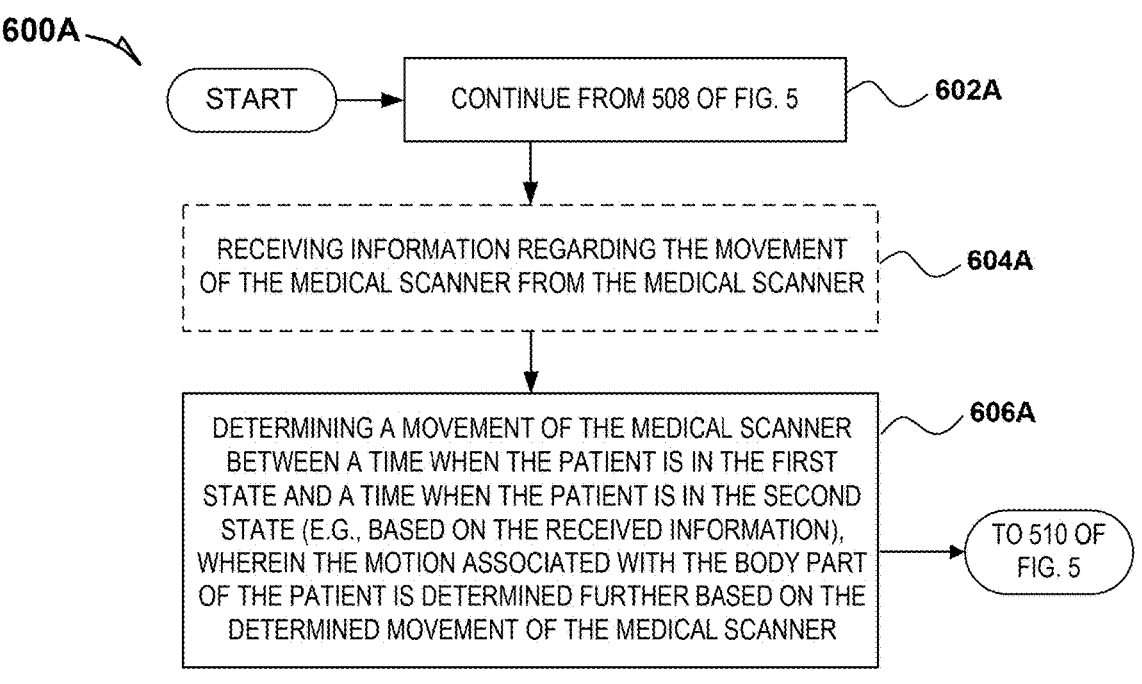

600A

START → CONTINUE FROM 508 OF FIG. 5 — 602A

RECEIVING INFORMATION REGARDING THE MOVEMENT OF THE MEDICAL SCANNER FROM THE MEDICAL SCANNER — 604A

DETERMINING A MOVEMENT OF THE MEDICAL SCANNER BETWEEN A TIME WHEN THE PATIENT IS IN THE FIRST STATE AND A TIME WHEN THE PATIENT IS IN THE SECOND STATE (E.G., BASED ON THE RECEIVED INFORMATION), WHEREIN THE MOTION ASSOCIATED WITH THE BODY PART OF THE PATIENT IS DETERMINED FURTHER BASED ON THE DETERMINED MOVEMENT OF THE MEDICAL SCANNER — 606A

START → CONTINUE FROM 606A OF FIG. 6A — 602B

DETERMINING A PRELIMINARY MOTION ASSOCIATED WITH THE BODY PART OF THE PATIENT BASED ON THE FIRST PLURALITY OF FEATURES AND THE SECOND PLURALITY OF FEATURES — 604B

DETERMINING THE PRELIMINARY MOTION IN MULTIPLE DIMENSIONS WHEREIN THE MOVEMENT OF THE MEDICAL SCANNER IS SUBTRACTED FROM AT LEAST ONE OF THE MULTIPLE DIMENSIONS — 606B

DETERMINING THE MOTION ASSOCIATED WITH THE BODY PART OF THE PATIENT BY SUBTRACTING THE MOVEMENT OF THE MEDICAL SCANNER FROM THE PRELIMINARY MOTION ASSOCIATED WITH THE BODY PART OF THE PATIENT — 608B

MOTION DETECTION ASSOCIATED WITH A BODY PART

BACKGROUND

Motion detection can play an important role in the medical imaging field because the ability to ascertain and track the motions/movements of a patient may be crucial to the success of many medical applications or procedures including, for example, computed tomography (CT) or magnetic resonance imaging (MRI) scanning. Any movement of the patient (e.g., inside a medical scanner) that is not taken into consideration by the scanner can significantly reduce the scan quality of the CT or MRI. However, a medical environment may include many moving elements (e.g., a movement of a CT or MRI scan bed) that are not related to any movement made by the patient (e.g., the patient moves their arm). Some motion detection methods are based on human body landmark detection and, therefore, they may be difficult to implement in enclosed medical environments where only some parts of the patient's body are visible (e.g., during MRI scanning). Accordingly, systems, methods, and instrumentalities are desired for improving the quality and efficiency of conventional motion detection techniques for use in certain enclosed medical environments.

SUMMARY

Described herein are systems, methods, and instrumentalities associated with detecting motion associated with a body part of a patient. An apparatus configured to perform the motion detection may include at least one processor configured to obtain, from an image sensor installed inside a medical scanner (e.g., an MRI scanner), a first image of the patient inside the medical scanner and a second image of the patient inside the medical scanner, wherein the first image may depict the patient in a first state and the second image may depict the patient in a second state. The at least one processor may also be configured to identify a first area (e.g., via a first bounding box), in the first image, that corresponds to a body part of the patient and also identify a second area (e.g., via a second bounding box), in the second image, that corresponds to the same body part of the patient. The at least one processor may be further configured to extract a first plurality of features (e.g., image features associated with pixel intensities, texture, etc.) from the first area of the first image and a second plurality of features from the second area of the second image, and to then determine a motion associated with the body part of the patient based at least on the first plurality of features and the second plurality of features. In some embodiments, the medical scanner may include a computer tomography (CT) scanner or a magnetic resonance imaging (MRI) scanner.

In some embodiments, the at least one processor may be further configured to determine the movement of the medical scanner between a time when the patient is in the first state and a time when the patient is in the second state, and the motion associated with the body part of the patient may be determined further based on the determined movement of the medical scanner. In some embodiments, the at least one processor may be further configured to receive information regarding the movement of the medical scanner from the medical scanner, and the movement of the medical scanner may be determined based on the received information.

In some embodiments, the at least one processor being configured to determine the motion associated with the body part of the patient further based on the determined movement of the medical scanner may include the at least one processor being configured to determine a preliminary motion associated with the body part of the patient based on the first plurality of features and the second plurality of features, and to then determine the motion associated with the body part of the patient by subtracting the movement of the medical scanner from the preliminary motion associated with the body part of the patient. In some embodiments, the at least one processor may be configured to determine the preliminary motion in multiple dimensions and subtract the movement of the medical scanner from at least one of the multiple dimensions.

In some embodiments, the at least one processor being configured to determine the motion associated with the body part of the patient based at least on the first plurality of features and the second plurality of features may include the at least one processor being configured to determine corresponding features from the first plurality of features and the second plurality of features, and to then determine the motion associated with the body part of the patient based on differences between the corresponding features. In some embodiments, the at least one processor being configured to determine the corresponding features from the first plurality of features and the second plurality of features may include the at least one processor being configured to identify corresponding pixels in the first area of the first image and the second area of the second image that are associated with the body part of the patient, and to then determine the corresponding features from the first plurality of features and the second plurality of features by selecting respective features from the first plurality of features and the second plurality of features that are associated with the identified pixels.

In some embodiments, the at least one processor may be configured to identify the first area in the first image and the second area in the second image that correspond to the body part of the patient based on a first machine-learning (ML) model. In some embodiments, the at least one processor may be further configured to extract the first plurality of features from the first area of the first image and the second plurality of features from the second area of the second image based on the first ML model or a second ML model.

In some embodiments, the image sensor installed inside the medical scanner may include a color image sensor. The first image of the patient may include a first color image of the patient, and the second image of the patient may include a second color image of the patient.

BRIEF DESCRIPTION OF THE DRAWINGS

A more detailed understanding of the examples disclosed herein may be had from the following descriptions, given by way of example in conjunction with the accompanying drawings.

FIG. 5 shows a flow diagram illustrating example operations that may be performed for detecting a motion associated with a body part of a patient based on first and second images depicting the patient inside a medical scanner.

FIG. 6A shows a flow diagram illustrating an example method for determining the motion of a body part of a patient based on a movement of a medical scanner between a time when a first image of the patient was captured and a time when a second image of the patient was captured.

FIG. 6B shows a flow diagram illustrating an example method for determining the motion of a body part of a patient based on a preliminary motion associated with the body part of the patient and the movement of a medical scanner.

DETAILED DESCRIPTION

The present disclosure is illustrated by way of example, and not by way of limitation, in the figures of the accompanying drawings.

Figure 1:
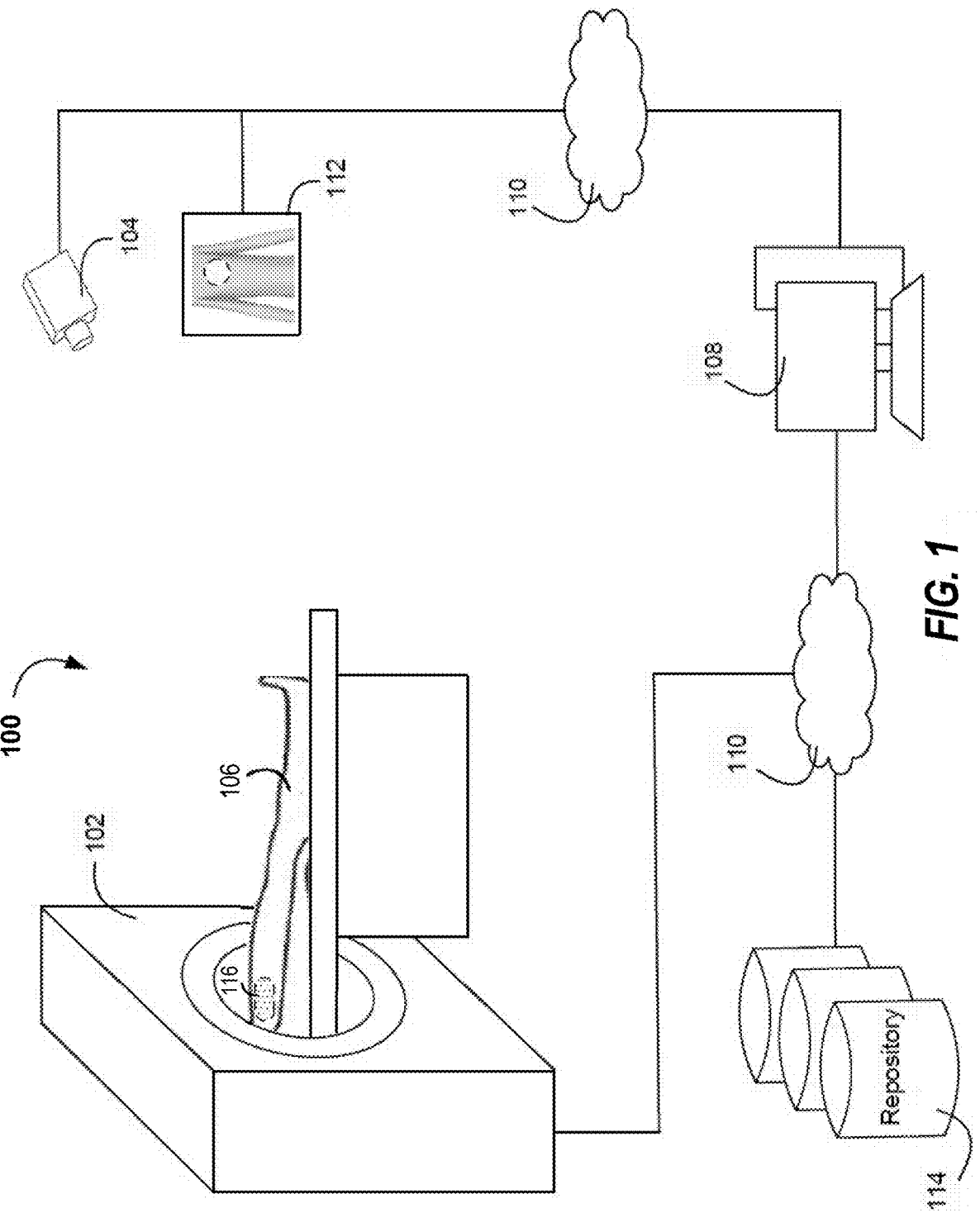
FIG. 1 shows a diagram illustrating an example, in accordance with one or more embodiments disclosed herein, of utilizing the methods and instrumentalities described herein to detect a motion associated with a body part of a patient.

FIG. 1 is a diagram illustrating an example environment 100, in accordance with one or more embodiments disclosed herein, that may utilize the methods and instrumentalities described herein to detect a motion associated with a body part of a patient 106.

As shown in the figure, the environment 100 may be configured to provide a medical scan or imaging procedure conducted using a medical scanner 102 (e.g., a computed tomography (CT) scanner, a magnetic resonance imaging (MRI) machine, a positron emission tomography (PET) scanner, an X-ray machine, etc.), even though the environment 100 may also be adapted to provide other types of healthcare services including, for example, radiation therapy, surgery, etc. For example, the medical scan or imaging procedure conducted using the medical scanner 102 may include an MRI scan of an internal organ 116 of the patient 106 (e.g., the heart of patient 106).

The environment 100 may include at least one sensing device 104 (e.g., an image capturing device) configured to capture images (e.g., a sequence of images) of the patient 106, for example, in front of the medical scanner 102, lying on a scan or treatment bed, etc. The sensing device 104 may comprise one or more sensors including one or more cameras (e.g., digital color cameras), one or more red, green and blue (RGB) sensors, one or more depth sensors, one or more RGB plus depth (RGB-D) sensors, one or more thermal sensors such as infrared (FIR) or near-infrared (NIR) sensors, and/or the like. Depending on the type of sensors used, the images captured by the sensing device 104 may include, for example, one or more images from a video sequence of the patient 106 taken by a camera, one or more 2D RGB images generated by an RBG sensor, etc. Although the sensing device 104 is shown in FIG. 1 as being located away from the medical scanner 102, the sensing device 104 may be installed or placed at various distinct locations of the environment 100, such as within the medical scanner 102 in order to capture images of the patient 106 inside the medical scanner 102 (e.g., without obstruction or blockage).

The sensing device 104 may include one or more processors configured to process the images of the patient 106 captured by any of the sensors described herein. Additionally or alternatively, the environment 100 may include a processing device 108 communicatively coupled to the sensing device 104 and configured to process the images of the patient 106 captured by the sensing device 104. The processing device 108 may be coupled to the sensing device 104 (e.g., to the sensors comprised in the sensing device 104), for example, via a communication network 110, which may be a wired or wireless communication network. In response to receiving the images of the patient 106, the sensing device 104 and/or the processing device 108 may analyze the images (e.g., at a pixel level) in order to determine various anatomical characteristics of the patient 106. For example, determining the various anatomical characteristics of the patient 106 may include identifying areas (e.g., via respective bounding boxes) in the images that correspond to body parts of the patient 106 (e.g., a head, an arm, a leg, etc.) and extracting features (e.g., sparse features associated with the corresponding body parts) from the identified areas in the images. In example embodiments (described below), the sensing device 104 and/or the processing device 108 may perform motion detection associated with the corresponding body parts of patient 106 based on images (e.g., a video or image sequence) of the patient 106 captured by an image sensor (e.g., sensing device 104) installed inside the medical scanner 102 (e.g., inside an MRI scanner).

In response to receiving the images of the patient 106, the sensing device 104 and/or the processing device 108 may provide (e.g., via display device 112) a user interface for viewing the images (which may include images of the patient 106 inside the medical scanner 102) and adjusting values associated with the anatomical characteristics (e.g., identified areas in the images that correspond to body parts) of the patient 106 as determined from the one or more images of the patient 106. In this way, the environment 100 may protect itself against obvious errors by providing a human (e.g., a clinician) with the ability to adjust/correct values associated with the automatically determined anatomical characteristics of the patient 106 (e.g., modify the dimensions of the identified areas). The adjusted/corrected values may then be used to extract features (e.g., sparse features) from the modified areas in the images of the patient 106 and perform motion detection associated with the corresponding body parts of patient 106 based on the extracted features.

The motion detection associated with the corresponding body parts of patient 106 performed by the sensing device 104 and/or the processing device 108 may be used to facilitate a plurality of downstream medical applications and services including, for example, patient positioning, medical protocol design, unified or correlated diagnoses and treatments, patient monitoring, surgical navigation, etc. For example, the processing device 108 may determine, based on the motion detection associated with the corresponding body parts of patient 106, whether the state of the patient 106 (e.g., a body shape, position and/or pose) meets the requirements of a predetermined protocol (e.g., while the patient 106 is inside the medical scanner 102), and provide real-time confirmation or adjustment instructions (e.g., via the display device 112), to help the patient 106 get into a desired state (e.g., front, back or side facing). The processing device 108 may also control (e.g., adjust) one or more operating parameters of the medical scanner 102 such as the height of the scan bed based on the state (e.g., a body shape, position and/or pose) of the patient 106 as indicated by the motion detection associated with the corresponding body parts of patient 106.

The sensing device 104 and/or the processing device 108 may be coupled with a medical record repository in storage device(s) 114 configured to store patient medical records including scan images of the patient 106 obtained through other imaging modalities (e.g., CT, MR. X-ray, SPECT, PET, etc.). The sensing device 104 and/or the processing device 108 may analyze the medical records of patient 106 stored in the repository in storage device(s) 114 using the state of the patient 106 (e.g., based on the motion detection associated with the corresponding body parts of patient 106) as a reference in order to obtain a more accurate understanding of any medical conditions of patient 106. For instance, the processing device 108 may examine scan images of the patient 106 from the repository in storage device(s) 114 in which the patient is in the same (or very similar) state as in the captured images of patient 106 in order to allow the scan images to be presented (e.g., via display device 112) and analyzed with reference to the anatomical characteristics (e.g., identified areas in the images that correspond to body parts) of the patient 106.

Figure 2:
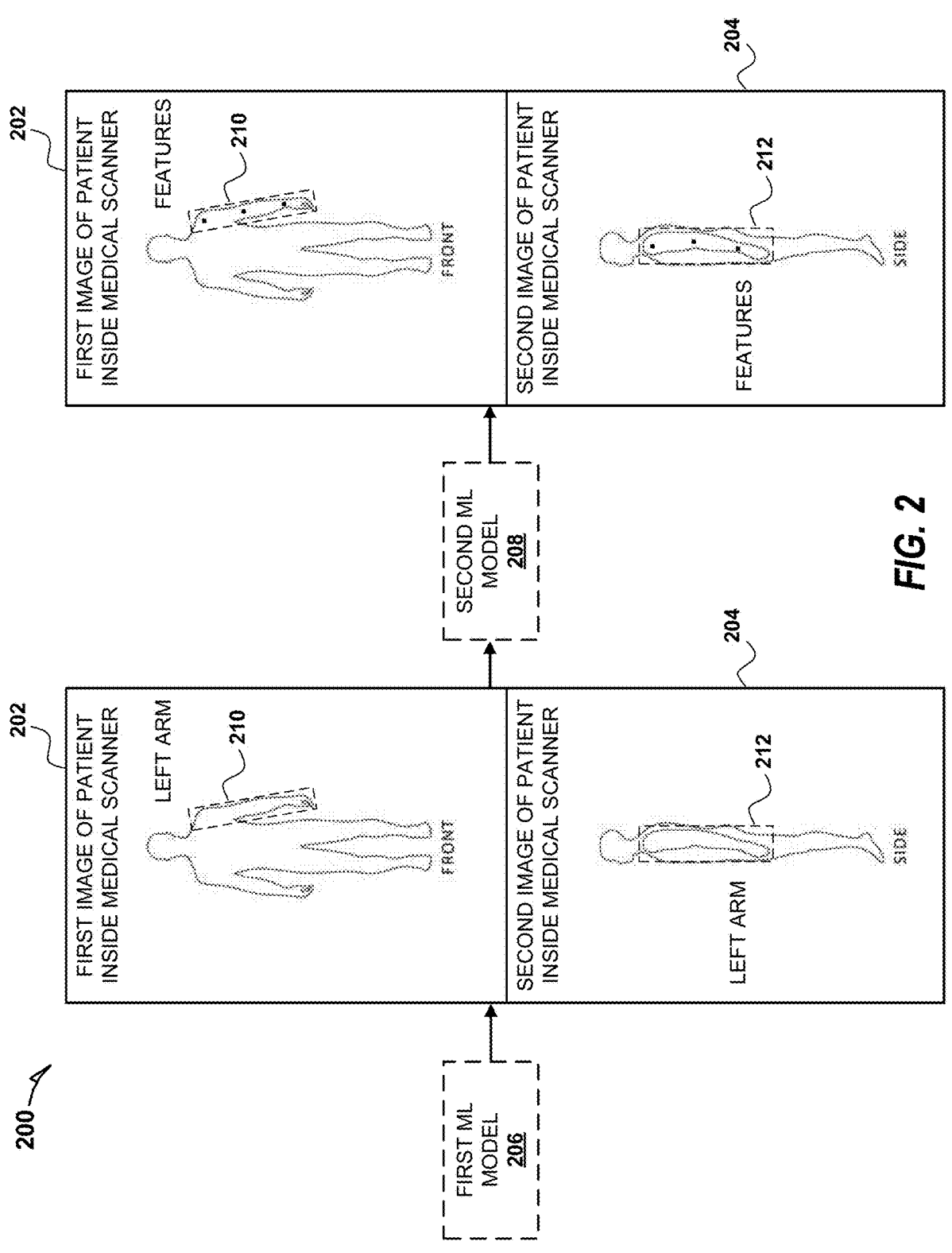
FIG. 2 shows a simplified block diagram illustrating how areas corresponding to a body part of a patient may be identified in first and second images depicting the patient inside a medical scanner and how features may be extracted from the identified areas.

FIG. 2 shows a simplified block diagram illustrating how areas corresponding to the body part of the patient 106 may be identified in first and second images depicting the patient inside a medical scanner (e.g., medical scanner 102 of FIG. 1) and features may be extracted from the identified areas.

An apparatus 200, comprising one or more processors, may be configured to obtain, from an image sensor (e.g., image sensor 104 of FIG. 1) installed inside the medical scanner 102, a first image 202 of the patient 106 inside the medical scanner 102 and a second image 204 of the patient 106 inside the medical scanner 102, wherein the first image 202 may depict the patient 106 in a first state (e.g., front-facing) and the second image 204 may depict the patient 106 in a second state (e.g., side facing). The apparatus 100 may also be configured to identify (e.g., using a first machine learning model 206) a first area 210, in the first image 202, that corresponds to a body part (e.g., the left arm) of the patient 106 and also identify a second area 212, in the second image 204, that corresponds to the same body part (e.g., the left arm) of the patient 106.

The apparatus 200 may be further configured to extract (e.g., using the first machine learning model 206 or a second machine learning model 208) a first plurality of features (e.g., representing image properties such as pixel intensities and/or textures associated with the corresponding body part such as a shoulder, elbow and/or wrist associated with the left arm of the patient 106) from the first area 210 of the first image 202 and a second plurality of features from the second area 212 of the second image 204. The apparatus 200 may be configured to then determine a motion associated with the body part (e.g., the left arm) of the patient 106 based at least on the first plurality of features and the second plurality of features.

In some embodiments, the apparatus 200 may be configured to determine the motion associated with the body part (e.g., the left arm) of the patient 106 by determining corresponding features from the first plurality of features and the second plurality of features (e.g., shoulder, elbow and wrist features associated with the left arm of patient 106), and then determining the motion associated with the body part of the patient based on differences between the corresponding features. For example, the apparatus 200 may compare the respective locations of the shoulder, elbow, and wrist features associated with the left arm of the patient 106 in each of the first image 202 and second image 204 of the patient 106 inside the medical scanner 102 and then determine a motion associated the left arm of patient 106 based on differences in the locations of corresponding features (e.g., locations of the elbow feature) in each image of the patient 106 inside the medical scanner 102.

In some embodiments, the apparatus 200 may be configured to determine the corresponding features (e.g., shoulder, elbow and wrist features associated with the left arm of patient 106) from the first plurality of features and the second plurality of features by identifying corresponding pixels in the first area 210 of the first image 202 and the second area 212 of the second image 204 that are associated with the body part (e.g., the left arm) of the patient 106, and to then determine the corresponding features from the first plurality of features and the second plurality of features by selecting respective features from the first plurality of features and the second plurality of features that are associated with the identified pixels.

As noted above, in some embodiments, the apparatus 200 may be configured to identify the first area 210 in the first image 202 and the second area 212 in the second image 204 that correspond to the body part (e.g., the left arm) of the patient 106 based on the first machine-learning (ML) model 206 and, in some embodiments, the apparatus 100 may be further configured to extract the first plurality of features from the first area 210 in the first image 202 and the second plurality of features from the second area 212 in the second image 204 based on the first ML model 206 or a second ML model 208 (e.g., the identification of areas 210 and 212, and the extraction of features from those areas may be performed based on a same ML model or based on different ML models).

Also, as noted above, in some embodiments, the medical scanner 102 may include a computed tomography (CT) scanner or a magnetic resonance imaging (MRI) scanner. In some embodiments, the first image 202 and the second image 204 of the patient 106 inside the medical scanner 102 may comprise sequential images from a video sequence captured, for example, by the sensing device 104 of apparatus 100 of FIG. 1. Furthermore, information regarding the determined motion associated with the body part (e.g., the left arm) of the patient 106 may be provided to a receiving device (e.g., which may be coupled to processing device 108 of FIG. 1 via network 110) which may control (e.g., adjust) one or more operating parameters of medical equipment (e.g., the height of the scan bed of the medical scanner 102) based on the new state (e.g., side facing) of the patient 106. In some embodiments, the image sensor 104 installed inside the medical scanner 102 may include a color image sensor, the first image 202 of the patient 106 may include a first color image of the patient 106, and the second image 204 of the patient may include a second color image of the patient 106.

The machine learning (ML) model described herein (e.g., first machine learning model 206 and/or second machine learning model 208) may be implemented via an artificial neural network (ANN) such as a convolutional neural network (CNN). In example implementations, such an ANN may include one or more convolutional layers, one or more pooling layers, and/or one or more fully connected layers. Each of the convolutional layers may include a plurality of convolution kernels or filters configured to extract features from an input image, and the convolution operations may be followed by batch normalization and/or line or non-linear activation. The features extracted by the convolutional layers may be down-sampled through the pooling layers and/or the fully connected layers to obtain a feature map or vector representing the extracted features. In example implementations, the ANN may further include one or more un-pooling layers and one or more transposed convolutional layers. Through the un-pooling layers, the down-sampled features extracted from the input image may be up-sampled, and the up-sampled features may be further processed through the transposed convolution operations to derive a denser feature map. The denser feature map may then be used to predict (e.g., with a probability or confidence score) whether a pixel or voxel of the input image is part of a body part of a person depicted in the input image.

Figure 3:
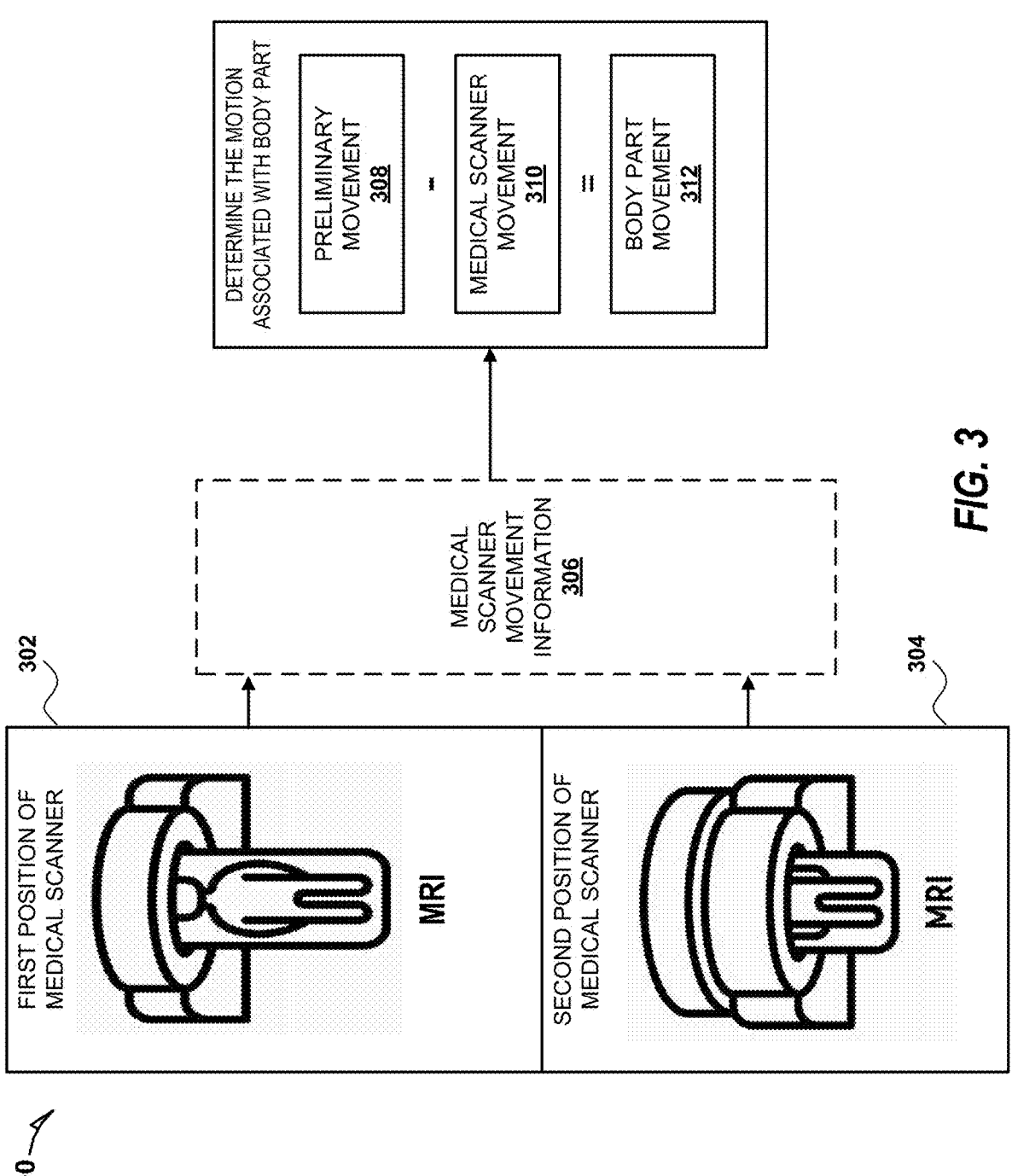
FIG. 3 shows a simplified block diagram illustrating example operations that may be associated with detecting a motion associated with a body part of a patient based on first and second images depicting the patient inside a medical scanner.

FIG. 3 shows a simplified block diagram 300 illustrating example operations that may be performed by the apparatus described herein (e.g., processing device 108 of FIG. 1) in association with detecting a motion associated with the body part (e.g., the left arm) of the patient 106 based on the first and second images 202 and 204 depicting the patient 106 inside the medical scanner 102. As shown in FIG. 3, the apparatus (e.g., processing device 108 of FIG. 1) may be configured to determine a movement of the medical scanner 102 between a time 302 (e.g., corresponding to first image 202 of FIG. 2) when the patient 106 is in the first state (e.g., front-facing) and a time 304 (e.g., corresponding to second image 204) when the patient 106 is in the second state (e.g., side facing), and the motion associated with the left arm of the patient 106 may be determined further based on the determined movement of the medical scanner 102. For example, the apparatus described herein may determine the movement of the medical scanner 102 based on images (e.g., captured by a sensor 104) depicting the bed of the medical scanner 102 (e.g., an MRI scanner), on which patient 106 is positioned, moving further into the medical scanner 102. As another example, the apparatus described herein may be further configured to receive information 306 regarding the movement of the medical scanner 102 from the medical scanner 102 and determine the movement of the medical scanner 102 based on the received information 306. In the latter example, the medical scanner 102 may transmit the information 306 to the apparatus via the network 110 of FIG. 1.

In some embodiments, the apparatus may be configured to determine the motion associated with the body part (e.g., left arm) of the patient 106 by determining a preliminary motion associated with the left arm of the patient 106 (e.g., preliminary movement 308) based on the first plurality of features and the second plurality of features (e.g., as described above), and to then determine the motion associated with the left arm of the patient 106 (e.g., body part movement 312) by subtracting the movement of the medical scanner 102 (medical scanner movement 310 as indicated by the information 306) from the preliminary movement 308 associated with the body part of the patient 106. In some embodiments, the apparatus may be configured to determine the preliminary movement 308 in multiple dimensions (e.g., using x, y, and z coordinates) and subtract the medical scanner movement 310 from the preliminary movement 308 in at least one of the multiple dimensions (e.g., along of the movement direction of the scanner bed).

Figure 4:
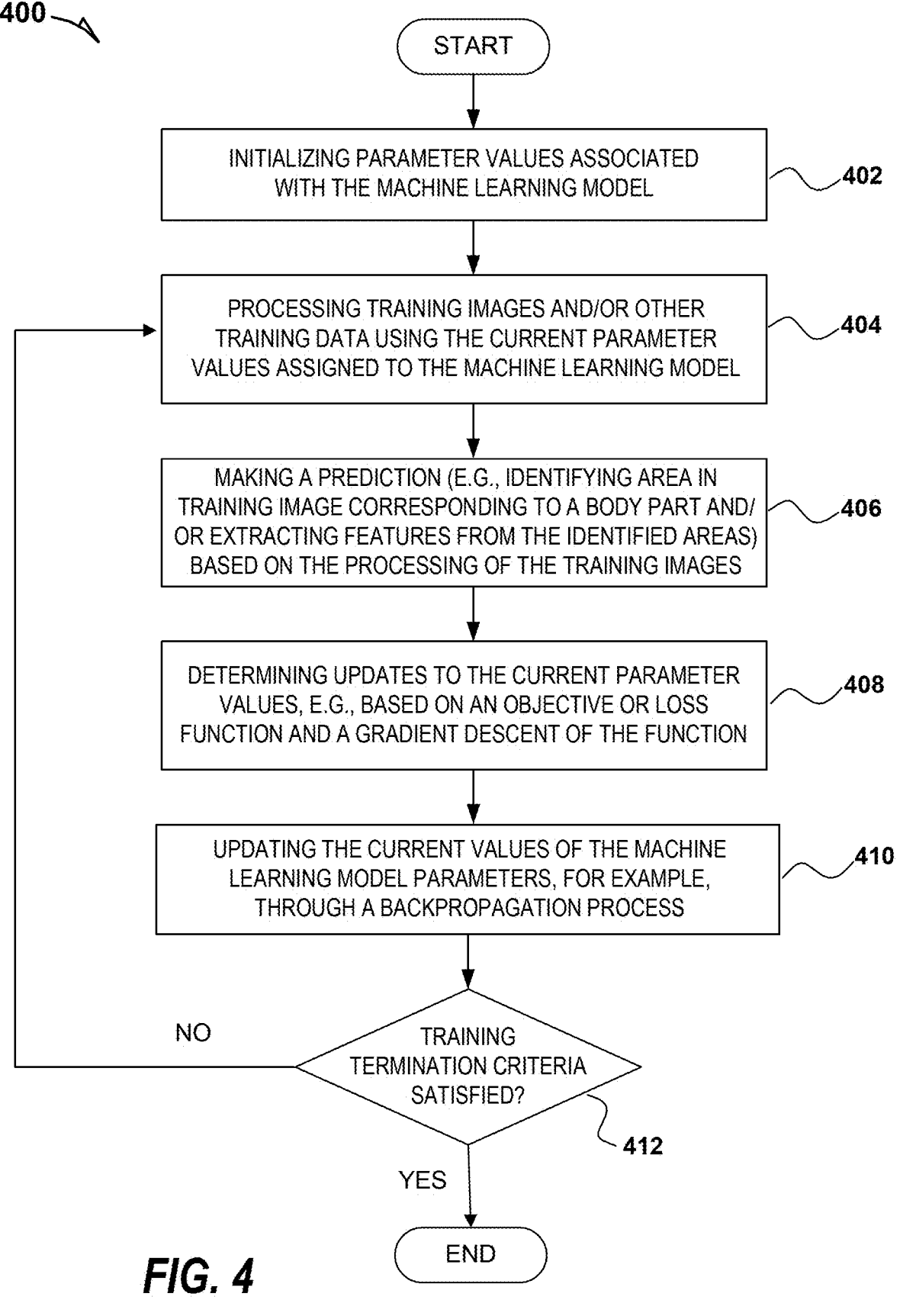
FIG. 4 shows a flow diagram illustrating how a machine learning (ML) model may be trained to identify image areas corresponding to a body part of a patient and to extract features from the identified image areas.

FIG. 4 shows a flow diagram 400 illustrating how a machine learning (ML) model (e.g., model 204 and/or 206 of FIG. 2, which may be implemented and/or learned using an artificial neural network) may be trained to identify image areas (e.g., areas 210 and 212 of FIG. 2) corresponding to the body part (e.g., the left arm) of the patient 106 and to extract features from the identified image areas.

The training process 400 may be performed by a system of one or more computers. At 402, the system may initialize the operating parameters of the machine learning model (e.g., weights associated with various layers of the artificial neural network used to implement the machine learning model). For example, the system may initialize the parameters based on samples from one or more probability distributions or parameter values associated with a similar machine learning model.

At 404, the system may process training images and/or other training data, such as the captured images of a patient inside a medical scanner, using the current parameter values assigned to the machine learning model.

At 406, the system may make a prediction (e.g., identify area in training image corresponding to a body part of a patient and/or extract features from the identified areas) based on the processing of the training images.

At 408, the system may determine updates to the current parameter values associated with the machine learning model, e.g., based on an objective or loss function and a gradient descent of the function. As described herein, the objective or loss function may be designed to measure a difference between the prediction and ground truth. The objective function may be implemented using, for example, mean squared errors, L1 norm, etc., associated with the prediction and/or the ground truth.

At 410, the system may update the current values of the machine learning model parameters, for example, by back-propagating the gradient descent of the loss function through the artificial neural network. The learning process may be an iterative process, and may include a forward propagation process to predict an output (e.g., prediction) based on the machine learning model and the input data fed into the machine learning model, and a backpropagation process to adjust parameters of the machine learning model based on a gradience descent associated with a calculated difference between the desired output (e.g., ground truth) and the predicted output.

At 412, the system may determine whether one or more training termination criteria are satisfied. For example, the system may determine that the training termination criteria are satisfied if the system has completed a predetermined number of training iterations, or if the change in the value of the loss function between two training iterations falls below a predetermined threshold. If the determination at 412 is that the training termination criteria are not satisfied, the system may return to 404. If the determination at 412 is that the training termination criteria are satisfied, the system may end the training process 400.

After training, the system (e.g., a replica of the system) may receive new data inputs (e.g., new images of the patient 106 inside the scanner 102) associated with the task and determine, based on the trained machine learning model, an estimated output as a predicted outcome for the task (e.g., an output that identifies areas in the new images corresponding to a body part of the patient and/or extracts features from the identified areas).

FIG. 5 shows a flow diagram illustrating example operations that may be performed for detecting a motion associated with the body part (e.g., the left arm) of the patient 106 based on the first and second images 202 and 204 depicting the patient 106 inside the medical scanner 102.

Operation 502 may include obtaining (e.g., from an image sensor 104 installed inside the medical scanner 102) a first image 202 of the patient 106 inside the medical scanner 102 and a second image 204 of the patient 106 inside the medical scanner 102, wherein the first image 202 depicts the patient 106 in a first state (e.g., front-facing) and the second image 204 depicts the patient 106 in a second state (e.g., side facing).

Operation 504 may include identifying (e.g., using the first machine learning model 206 of FIG. 2) a first area 210, in the first image 202, that corresponds to a body part (e.g., the left arm) of the patient 106.

Operation 506 may include identifying (e.g., using the first machine learning model 206) a second area 212, in the second image 204, that corresponds to the same body part (e.g., the left arm) of the patient 106.

Operation 508 may include extracting (e.g., using the first machine learning model 206 or the second machine learning model 208 of FIG. 2) a first plurality of features (e.g., associated with the corresponding body part such as a shoulder, elbow and/or wrist associated with the left arm of the patient 106) from the first area 210 of the first image 202 and a second plurality of features (e.g., the shoulder, elbow and/or wrist features associated with the left arm of the patient 106) from the second area 212 of the second image 204.

Operation 510 may include determining a motion associated with the body part (e.g., the left arm) of the patient 106 based at least on the first plurality of features and the second plurality of features. As described above, respective locations of the shoulder, elbow and wrist features associated with the left arm of the patient 106 in each of the first image 202 and second image 204 of the patient 106 inside the medical scanner 102 may be compared and then the motion associated the left arm of patient 106 may be determined based on differences in the locations of corresponding features (e.g., locations of the elbow feature) in each image of the patient 106 inside the medical scanner 102.

FIG. 6A shows a flow diagram illustrating an example method 600A for determining the motion of the body part (e.g., the left arm) of the patient 106 based on a movement of the medical scanner 102 between a time when the first image 202 was captured (e.g., by a sensor 104 inside the medical scanner 102) and a time when the second image 204 was captured.

The method 600A may start and, at 602A, may continue from 508 of method 500 of FIG. 5 as described above.

At 604A, the method may include receiving information regarding the movement of the medical scanner 102 (e.g., information 306 of FIG. 3) from the medical scanner 102. For example, the medical scanner 102 may transmit the information 306 to the processing device 108 of apparatus 100 via the network 110 of FIG. 1. In examples (not shown in FIG. 6A), the method may include determining, at 604A, the movement of the medical scanner 102 by processing images (e.g., captured by sensor 104 of FIG. 1) that indicate the movement of the medical scanner.

At 606A, the method may include determining the movement of the medical scanner 102 between the time when the first image 202 was captured (e.g., by the sensor 104 inside the medical scanner 102) and the time when the second image 204 was captured (e.g., based on the received information 306) and further determining the motion of the left arm of the patient 106 based on the movement of the medical scanner 102. The method may then proceed to 510 of FIG. 5 as described above.

FIG. 6B shows a flow diagram illustrating an example method 600B for determining the motion of the body part (e.g., the left arm) of the patient 106 based on a preliminary motion associated with the body part of the patient 106 and the movement of the medical scanner 102.

The method 600B may start and, at 602B, may continue from 606A of method 600A of FIG. 6A as described above.

At 604B, the method may include determining a preliminary motion (e.g., preliminary movement 308 associated with the left arm of the patient 106) based on the first plurality of features and the second plurality of features (e.g., as described above).

At 606B, the method may include determining the preliminary movement 308 in multiple dimensions (e.g., using x, y, and z coordinates) and then subtracting the medical scanner movement 310 from the preliminary movement 308 (e.g., as described below) in at least one of the multiple dimensions.

At 608B, the method may include determining the motion associated with the left arm of the patient 106 (e.g., body part movement 312) by subtracting the movement of the medical scanner 102 (medical scanner movement 310 as indicated by the information 306 regarding the movement of the medical scanner 102) from the preliminary movement 308 associated with the body part of the patient 106 (e.g., possibly in multiple dimensions as noted above). The method may then proceed to 510 of FIG. 5 as described above.

For simplicity of explanation, the operations of the methods (e.g., performed by apparatus 100 of FIG. 1) are depicted and described herein with a specific order. It should be appreciated, however, that these operations may occur in various orders, concurrently, and/or with other operations not presented or described herein. Furthermore, it should be noted that not all operations that the apparatus is capable of performing are depicted in FIGS. 5 and 6A-6B or described herein. It should also be noted that not all illustrated operations may be required to be performed.

Figure 7:
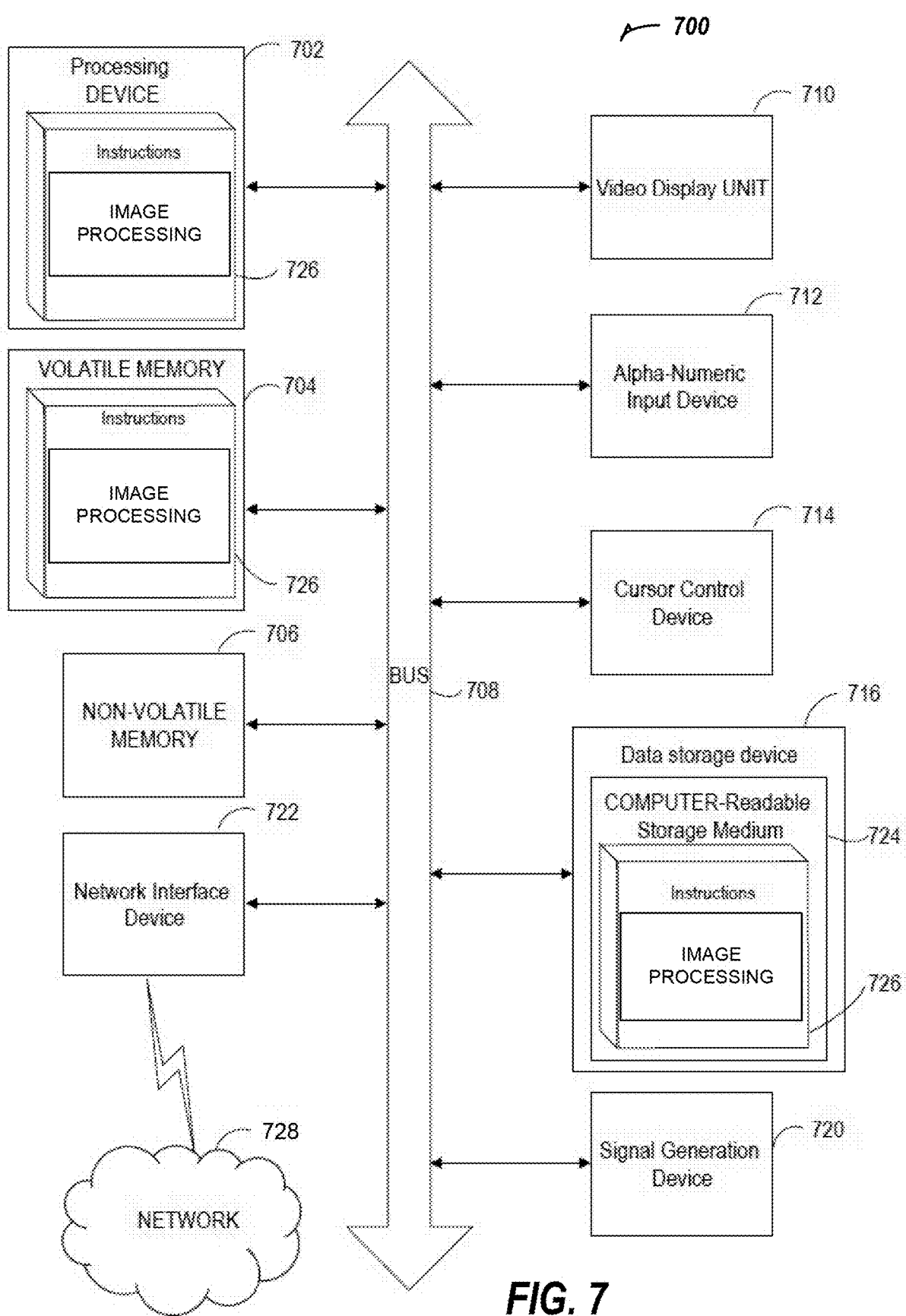
FIG. 7 is a simplified block diagram illustrating example components of an apparatus that may be configured to perform the tasks for detecting the motion associated with a body part of a patient based on first and second images depicting the patient inside a medical scanner.

FIG. 7 is a simplified block diagram illustrating an example computer apparatus 700 (e.g., part of processing device 108 of FIG. 1) that may be configured to perform the tasks for detecting the motion associated with the body part (e.g., the left arm) of the patient 106 based on the first and second images 202 and 204 depicting the patient 106 inside the medical scanner 102.

In embodiments, the computer apparatus 700 may be connected (e.g., via a network 728, such as a Local Area Network (LAN), an intranet, an extranet, or the Internet) to other remote computer systems. The computer apparatus 700 may operate in the capacity of a server or a client computer in a client-server environment, or as a peer computer in a peer-to-peer or distributed network environment. Computer apparatus 700 may be provided by a personal computer (PC), a tablet PC, a set-top box (STB), a Personal Digital Assistant (PDA), a cellular telephone, a web appliance, a server, a network router, a switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein.

Furthermore, the computer apparatus 700 may include a processing device 702, a volatile memory 704 (e.g., random access memory (RAM)), a non-volatile memory 706 (e.g., read-only memory (ROM) or electrically-erasable programmable ROM (EEPROM)), and a data storage device 716, which may communicate with each other via a bus 708. Processing device 702 may be provided by one or more processors such as a general purpose processor (such as, for example, a complex instruction set computing (CISC) microprocessor, a reduced instruction set computing (RISC) microprocessor, a very long instruction word (VLIW) microprocessor, a microprocessor implementing other types of instruction sets, or a microprocessor implementing a combination of types of instruction sets) or a specialized processor (such as, for example, an application specific integrated circuit (ASIC), a field programmable gate array (FPGA), a digital signal processor (DSP), or a network processor).

Computer apparatus 700 may further include a network interface device 722 (e.g., for interfacing with network 728), a video display unit 710 (e.g., an LCD), an alphanumeric input device 712 (e.g., a keyboard), a cursor control device 714 (e.g., a mouse), a data storage device 716, and/or a signal generation device 720. Data storage device 716 may include a non-transitory computer-readable storage medium 724 on which may store instructions 726 encoding any one or more of the image processing methods and/or functions described herein. Instructions 726 may also reside, completely or partially, within volatile memory 704 and/or within processing device 702 during execution thereof by computer apparatus 700, hence, volatile memory 704 and processing device 702 may also be machine-readable storage media.

While computer-readable storage medium 724 is shown in the illustrative examples as a single medium, the term "computer-readable storage medium" shall include a single medium or multiple media (e.g., a centralized or distributed database, and/or associated caches and servers) that store the one or more sets of executable instructions.

The term "computer-readable storage medium" used herein may include any tangible medium that is capable of storing or encoding a set of instructions for execution by a computer that cause the computer to perform any one or more of the methods described herein. The term "computer-readable storage medium" used herein may include, but not be limited to, solid-state memories, optical media, and magnetic media.

The methods, components, and features described herein may be implemented by discrete hardware components or may be integrated in the functionality of other hardware components such as ASICS, FPGAs, DSPs or similar devices. In addition, the methods, components, and features may be implemented by firmware modules or functional circuitry within hardware devices. Further, the methods, components, and features may be implemented in any combination of hardware devices and computer program components, or in computer programs.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

The invention claimed is:

1. An apparatus, comprising:
at least one processor configured to:
obtain, from a color image sensor installed inside a medical scanner, a first color image of a patient inside the medical scanner and a second color image of the patient inside the medical scanner, wherein the first color image depicts the patient in a first state and the second color image depicts the patient in a second state;
identify, using a first machine learning (ML) model, a first area in the first color image that corresponds to a body part of the patient;
identify, using the first ML model, a second area in the second color image that corresponds to the body part of the patient;
extract a first plurality of features from the first area of the first color image and a second plurality of features from the second area of the second color image;
determine a preliminary motion of the body part based on the first plurality of features and the second plurality of features;
calculate a movement of the medical scanner between a time when the patient is in the first state and a time when the patient is in the second state; and
determine a motion of the body part of the patient by subtracting the calculated movement of the medical scanner from the preliminary motion of the body part.

2. The apparatus of claim 1, wherein the medical scanner includes a computed tomography (CT) scanner or a magnetic resonance imaging (MRI) scanner.

3. The apparatus of claim 1, wherein the at least one processor is further configured to obtain one or more images of the medical scanner and calculate the movement of the medical scanner based on the one or more obtained images.

4. The apparatus of claim 1, wherein the at least one processor is further configured to receive information regarding the movement of the medical scanner from the medical scanner and calculate the movement of the medical scanner based on the received information.

5. The apparatus of claim 1, wherein the at least one processor is configured to determine the preliminary motion of the body part in multiple dimensions and subtract the movement of the medical scanner from at least one of the multiple dimensions.

6. The apparatus of claim 1, wherein the at least one processor being configured to determine the preliminary motion of the body part of the patient based on the first plurality of features and the second plurality of features comprises the at least one processor being configured to determine corresponding features from the first plurality of features and the second plurality of features, and determine the preliminary motion of the body part of the patient based on differences between the corresponding features.

7. The apparatus of claim 6, wherein the at least one processor being configured to determine the corresponding features from the first plurality of features and the second plurality of features comprises the at least one processor being configured to identify corresponding pixels in the first area of the first color image and the second area of the second color image that are associated with the body part of the patient, and determine the corresponding features from the first plurality of features and the second plurality of features by selecting respective features from the first plurality of features and the second plurality of features that are associated with the identified pixels.

8. The apparatus of claim 1, wherein the at least one processor is further configured to extract the first plurality of features from the first area of the first color image and the second plurality of features from the second area of the second color image using the first ML model or a second ML model.

9. A method for determining a motion associated with a body part of a patient, the method comprising:

obtaining, from a color image sensor installed inside a medical scanner, a first color image of the patient inside the medical scanner and a second color image of the patient inside the medical scanner, wherein the first color image depicts the patient in a first state and the second color image depicts the patient in a second state;

identifying, using a first machine learning (ML) model, a first area in the first color image that corresponds to the body part of the patient;

identifying, using the first ML model, a second area in the second color image that corresponds to the body part of the patient;

extracting a first plurality of features from the first area of the first color image and a second plurality of features from the second area of the second color image;

determining a preliminary motion of the body part of the patient based on the first plurality of features and the second plurality of features;

calculating a movement of the medical scanner between a time when the patient is in the first state and a time when the patient is in the second state; and determining the motion of the body part of the patient by subtracting the calculated movement of the medical scanner from the preliminary motion of the body part.

10. The method of claim 9, wherein the medical scanner includes a computed tomography (CT) scanner or a magnetic resonance imaging (MRI) scanner.

11. The method of claim 9, further comprising obtaining one or more images of the medical scanner, wherein the movement of the medical scanner is calculated based on the one or more obtained images.

12. The method of claim 9, further comprising receiving information regarding the movement of the medical scanner from the medical scanner, wherein the movement of the medical scanner is calculated based on the received information.

13. The method of claim 9, wherein the preliminary motion is determined in multiple dimensions and wherein the movement of the medical scanner is subtracted from at least one of the multiple dimensions.

14. The method of claim 9, wherein determining the preliminary motion associated with the body part of the patient based at least on the first plurality of features and the second plurality of features comprises determining corresponding features from the first plurality of features and the second plurality of features, and determining the preliminary motion associated with the body part of the patient based on differences between the corresponding features.

15. The method of claim 14, wherein determining the corresponding features from the first plurality of features and the second plurality of features comprises identifying corresponding pixels in the first area of the first color image and the second area of the second color image that are associated with the body part of the patient, and determining the corresponding features from the first plurality of features and the second plurality of features by selecting respective features from the first plurality of features and the second plurality of features that are associated with the identified pixels.

16. The method of claim 9, wherein the first plurality of features is extracted from the first area of the first color image and the second plurality of features is extracted from the second area of the second color image using the first ML model or a second ML model.

* * * * *